(12) United States Patent
Boroni et al.

(10) Patent No.: US 9,073,909 B2
(45) Date of Patent: Jul. 7, 2015

(54) [1,3]OXAZINES

(75) Inventors: Edilio Boroni, Basel (CH); Luca Gobbi, Muttenz (CH); Hans Hilpert, Muenchenstein (CH); Michael Honer, Zurich (CH); Dieter Murl, Basel (CH); Robert Narquizian, Zaessingue (FR); Alessandra Polara, Basel (CH)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/118,754

(22) PCT Filed: Jun. 4, 2012

(86) PCT No.: PCT/EP2012/060476
§ 371 (c)(1),
(2), (4) Date: Nov. 19, 2013

(87) PCT Pub. No.: WO2012/168175
PCT Pub. Date: Dec. 13, 2012

(65) Prior Publication Data
US 2014/0112867 A1   Apr. 24, 2014

(30) Foreign Application Priority Data
Jun. 7, 2011   (EP) .................................... 11168953

(51) Int. Cl.
| C07D 413/12 | (2006.01) |
| C07D 265/06 | (2006.01) |
| A61K 31/535 | (2006.01) |
| A61K 31/5355 | (2006.01) |

(52) U.S. Cl.
CPC ................................... *C07D 413/12* (2013.01)

(58) Field of Classification Search
CPC ............. A61K 31/535; A61K 31/5355; C07D 413/12; C07D 265/06
USPC ..................................... 544/88, 96; 514/228.8
See application file for complete search history.

(56) References Cited

U.S. PATENT DOCUMENTS 7,964,594 B1 *  6/2011  Banner et al. .............. 514/228.8
8,754,075 B2 *  6/2014  Hilpert et al. .............. 514/228.8

* cited by examiner

*Primary Examiner* — Kahsay Habte

(57) ABSTRACT

The present invention provides compounds of formula I

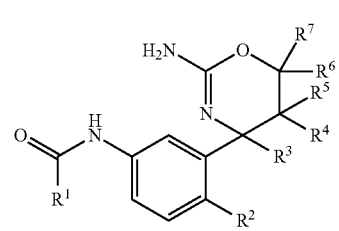

having BACE1 and/or BACE2 inhibitory activity, their manufacture, pharmaceutical compositions containing them and their use as therapeutically active substances. The active compounds of the present invention are useful in the therapeutic and/or prophylactic treatment of e.g. Alzheimer's disease and type 2 diabetes. The invention further provides a radio-labelled derivative thereof.

18 Claims, No Drawings

[1,3]OXAZINES

SUMMARY

The present invention is concerned with [1,3]oxazines having BACE1 and/or BACE2 inhibitory properties, their manufacture, pharmaceutical compositions containing them and their use as therapeutically active substances. The present invention further provides radio-labelled compounds of general formula I as BACE1 tracers, useful for the labelling and diagnostic imaging of the BACE1 functionality.

BACKGROUND ART

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 Jul. 19; 297(5580):353-6, Selkoe, Cell biology of the amyloid beta-protein precursor and the mechanism of Alzheimer's disease, *Annu Rev Cell Biol*. 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space, their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a pre-senilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci*. 2001 March; 4(3):231-2, Roberds et al., BACE knockout mice are healthy despite lacking the primary beta-secretase activity in brain: implications for Alzheimer's disease therapeutics, *Hum Mol Genet*. 2001 Jun. 1; 10(12):1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem*. 2007 Sep. 7; 282(36):26326). It is thus presumed that inhibitors of BACE1 activity can be useful agents for therapeutic intervention in Alzheimer's Disease (AD).

Type 2 diabetes (T2D) is caused by insulin resistance and inadequate insulin secretion from pancreatic β-cells leading to poor blood-glucose control and hyperglycemia (M Prentki & CJ Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, K G M M Alberti & J Shaw, "Global and societal implications of the diabetes epidemic" Nature 2001, 414, 782-787).

β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (L L Baggio & D J Drucker, "Therapeutic approaches to preserve islet mass in type 2 diabetes", Annu. Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes.

Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients. It is therefore an object of the present invention to provide selective BACE2 inhibitors. Such compounds are useful as therapeutically active substances, particularly in the treatment and/or prevention of diseases which are associated with the inhibition of BACE2.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

Objects of the present invention are novel compounds of formula I, their manufacture, medicaments based on a compound in accordance with the invention and their production as well as the use of compounds of formula I in the control or prevention of illnesses such as Alzheimer's disease and type 2 diabetes.

It has been found that the radio-labelled compounds of formula I can be used as PET (Positron Emission Tomography) radiotracer for the labelling and diagnostic molecular imaging of the BACE1 functionality, in particular [$^{11}$C]-labelled compounds of formula I. Molecular imaging is based on the selective and specific interaction of a molecular probe (e.g. a radiotracer) with a biological target (for instance a receptor, an enzyme, an ion channel or any other cellular component that is able to bind or retain the molecular probe) which is visualized through PET, nuclear magnetic resonance, near infrared or other methods. PET, a nuclear medical imaging modality, is ideally suited to produce three-dimensional images that provide important information, on the distribution of a biological target in a given organ, or on the metabolic activity of such organ or cell or on the ability of a drug to enter such organ, bind to a biological target and/or modify biological processes. Since PET is a non-invasive imaging technique it can be used to investigate the pathophysiology of a disease and the action of drug on a given molecular target or cellular processes in humans and in animals. The availability of a PET radiotracer specific for a given molecular target can facilitate drug development and the understanding of the mechanism of action of a drug. In addition, a PET radiotracer can facilitate diagnosis of a disease by demonstrating pathophysiological changes taking place as a consequence of the disease.

The human brain is a complex organ, consisting of millions of intercommunicating neurons. The understanding of abnormalities relating to diseases is the key to the future development of effective diagnosis and novel therapeutics. The study of biochemical abnormalities in human is rapidly becoming an essential and integral component of drug discovery and development process. Traditionally, the discovery and development of new drugs have been performed with a heavy emphasis on in vitro techniques to select promising lead candidates which are subsequently tested in living animals prior to human administration. Because in vitro systems reflect only part of the complexity of living systems and in vivo animal models of human disease are often only an approximation of human pathology, there is growing realization that a robust understanding of drug-receptor interaction in living man at an early stage in this process will be a major driving force in further enhancing the efficient and timely discovery and development of novel therapeutics. Over recent years, there has been a growing use of human medical imaging to assess pathologies, disease processes and drug action. These imaging modalities include PET, MRI, CT, ultrasound, EEG, SPECT and others (*British Medical Bulletin,* 2003, 65, 169-177). Therefore, the use of non-invasive imaging modalities, e.g. PET is an invaluable tool for the development of drugs in the future. Non-invasive nuclear imaging techniques can be used to obtain basic and diagnostic information about the physiology and biochemistry of a variety of living subjects. These techniques rely on the use of sophisticated imaging instrumentation that is capable of detecting radiation emitted from radiotracers administered to such living subjects. The information obtained can be reconstructed to provide planar and tomographic images that reveal distribution of the radiotracer as a function of time. The use of radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject. Currently, radiotracers are available for obtaining useful information concerning cardiac function, myocardial blood flow, lung perfusion, liver function, brain blood flow, regional brain glucose and oxygen metabolism (WO2007/041025). Furthermore, PET imaging provides a non-invasive and quantitative assay of normal and abnormal neurochemistry in human at an early stage of the drug development to enhance the efficient and effective discovery of therapeutics. Tracer doses of labeled compounds enable the early evaluation of novel drugs: bio-distribution studies; receptor occupancy studies to optimize drug-dosing regime and characterizing downstream responses of drug action. Understanding disease mechanisms in human using non-invasive techniques is intimately connected with future developments in the diagnosis and management of diseases and of novel therapeutics.

The radionuclides commonly used in PET include $^{11}$C, $^{13}$N, $^{15}$O and $^{18}$F. In principle, it is possible to label all drug analogs with a pet nuclide, but only a few are found applicable as imaging agents in vivo in humans. The radioactive half-time of $^{11}$C, $^{13}$N, $^{15}$O and $^{18}$F are 20, 10, 2 and 110 min, respectively. These short half-lives endow a number of advantages to their use as tracers to probe biological processes in vivo using PET. Repeat studies in the same subject within the same day are made possible. PET is being increasingly used as a tool to determine drug-dose-enzyme/receptor occupancy relationships in well-defined compounds. The use of PET radiotracers that specifically bind to the target receptor or enzyme can provide information about the ability of a drug to enter the brain and bind to the target site: the degree of occupancy of the target site produced by a given dose of drug, the time-course of occupancy, and the relative plasma and tissue kinetics of the drug in question.

Occupancy studies are performed with PET radiotracers which are usually not identical to the drug candidate under study (British Medical Bulletin, 2003, 65, 169-177).

Further objects of the present invention are radio-labelled inhibitors of general formula I as BACE1 tracer, useful for the labelling and diagnostic imaging of the BACE1 functionality.

TECHNICAL FIELD

The present invention provides a compound of formula I,

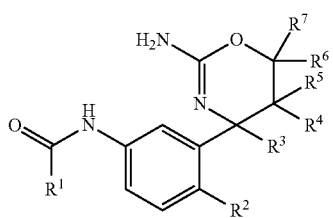

wherein the substituents and variables are as described below and in the claims, or a pharmaceutically acceptable salt thereof or a radio-labelled form thereof.

The present compounds have Asp2 (β-secretase, BACE1 or Memapsin-2) inhibitory activity and can therefore be used in the therapeutic and/or prophylactic treatment of diseases and disorders characterized by elevated β-amyloid levels and/or β-amyloid oligomers and/or β-amyloid plaques and further deposits, particularly Alzheimer's disease. And/or the present compounds have BACE2 inhibitory activity and can therefore be used in the therapeutic and/or prophylactic treatment of diseases and disorders such as type 2 diabetes and other metabolic disorders. The present invention further provides radio-labelled inhibitors of general formula I as BACE1 tracer, useful for the labelling and diagnostic imaging of the BACE1 functionality.

The present invention further provides radio-labelled compounds of general formula I as BACE1 tracer, useful for the labelling and diagnostic imaging of the BACE1 functionality.

DETAILED DESCRIPTION OF THE INVENTION

Object of the present invention are compounds of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with inhibition of BACE1 and/or BACE2 activity, such as Alzheimer's disease and type 2 diabetes. Furthermore, the formation, or formation and deposition, of β-amyloid plaques in, on or around neurological tissue (e.g., the brain) are inhibited by the present compounds by inhibiting the Aβ production from APP or an APP fragment.

The present invention further provides radio-labelled compounds of general formula I as BACE1 tracers, useful for the labelling and diagnostic imaging of the BACE1 functionality.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which can be linear or branched, with single or multiple branching, whereby the alkyl group in general comprises 1 to 6 carbon atoms, for example, methyl (Me), ethyl (Et), propyl, isopropyl (i-propyl), n-butyl, i-butyl (iso-butyl), 2-butyl (sec-butyl), t-butyl (tert-butyl) and the like. Particular alkyl groups are groups with 1 to 4 carbon atoms. Most particular is methyl.

The term "$C_{2-6}$-alkenyl" denotes a monovalent linear or branched saturated hydrocarbon group of 2 to 6 carbon atoms, in particular from 2 to 4 carbon atoms, and comprising one, two or three double bonds. Examples of alkenyl include ethenyl, propenyl and iso-butenyl.

The term "halogen-$C_{2-6}$-alkenyl", alone or in combination with other groups, refers to $C_{2-6}$-alkenyl as defined herewithin, which is substituted by one or multiple halogen as defined herein, particularly 1 halogen, in particular F, e.g. fluoro-ethenyl.

The term "$C_{1-6}$-alkoxy-$C_{2-6}$-alkenyl", alone or in combination with other groups, refers to $C_{2-6}$-alkenyl as defined herewithin, which is substituted by one or multiple $C_{1-6}$-alkoxy as defined herein, particularly 1 $C_{1-6}$-alkoxy, e.g. methoxy-ethenyl.

The term "$C_{2-6}$-alkynyl" denotes a monovalent linear or branched saturated hydrocarbon group of 2 to 6 carbon atoms, in particular from 2 to 4 carbon atoms, and comprising one or two triple bonds. Examples of alkynyl include ethynyl, propynyl, prop-2-ynyl, n-butynyl and iso-butynyl.

The term "halogen-$C_{2-6}$-alkynyl", alone or in combination with other groups, refers to $C_{2-6}$-alkynyl as defined herewithin, which is substituted by one or multiple halogen as defined herein, particularly 1 halogen, in particular F, e.g. fluoro-ethynyl.

The term "$C_{1-6}$-alkoxy-$C_{2-6}$-alkynyl", alone or in combination with other groups, refers to $C_{2-6}$-alkynyl as defined herewithin, which is substituted by one or multiple $C_{1-6}$-alkoxy as defined herein, particularly 1 $C_{1-6}$-alkoxy, e.g. methoxy-ethynyl.

The term "halogen", alone or in combination with other groups, denotes chloro (Cl), iodo (I), fluoro (F) and bromo (Br). Particular "halogen" is F.

The term "heteroaryl", alone or in combination with other groups, refers to an aromatic carbocyclic group having a single 4 to 8 membered ring or multiple condensed rings comprising 6 to 14, more particularly 6 to 10, ring atoms and containing 1, 2 or 3 heteroatoms individually selected from N, O and S, in particular 2 N, in which group at least one heterocyclic ring is aromatic. Examples of "heteroaryl" include benzofuryl, benzoimidazolyl, benzooxazinyl, benzothiazinyl, benzothiazolyl, benzothienyl, benzotriazolyl, furyl, imidazolyl, indazolyl, indolyl, isoquinolinyl, isothiazolyl, isoxazolyl, oxazolyl, pyrazinyl, pyrazolyl (pyrazyl), pyrazolo[1,5-a]pyridinyl, pyridazinyl, pyridinyl, pyrimidinyl, pyrrolyl, quinolinyl, tetrazolyl, thiazolyl, thienyl, triazolyl and the like. Particular is pyrazinyl. Specific is pyrazin-2-yl.

The term "$C_{1-6}$-alkoxy", alone or in combination with other groups, stands for an —O-lower alkyl radical which can be linear or branched, with single or multiple branching, whereby the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), iso-pentyloxy (i-pentyloxy) and the like. Particular are groups with 1 to 4 carbon atoms. Most particular is methoxy.

The term "$C_{2-6}$-alkenyl-$C_{1-6}$-alkoxy", alone or in combination with other groups, refers to $C_{1-6}$-alkoxy as defined herewithin, which is substituted by one $C_{2-6}$-alkenyl as defined herein. Examples are ethenyl-ethoxy, ethenyl-methoxy and the like.

The term "$C_{2-6}$-alkynyl-$C_{1-6}$-alkoxy", alone or in combination with other groups, refers to $C_{1-6}$-alkoxy as defined herewithin, which is substituted by one $C_{2-6}$-alkynyl as defined herein. Examples are ethynyl-ethoxy, ethynyl-methoxy and the like.

The term "$C_{2-6}$-alkynyl-$C_{1-6}$-alkoxy-pyrazinyl", alone or in combination with other groups, refers to a pyrazinyl ring, which is substituted by one $C_{2-6}$-alkynyl-$C_{1-6}$-alkoxy-group as defined herein. A particular example is 5-but-2-ynyloxy-pyrazinyl.

The term "aryl" denotes a monovalent aromatic carbocyclic mono- or bicyclic ring system comprising 6 to 10 carbon ring atoms. Examples of aryl moieties include phenyl and naphthyl. Specific is phenyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Particular are formic acid, trifluoroacetic acid and hydrochloric acid. Most particular is hydrochloric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-\log$ Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particular, more particular and most particular definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product can not necessarily result directly from the combination of two reagents which were initially added, i.e., there can be one or more intermediates which are produced in the mixture which ultimately leads to the formation of the indicated and/or the desired product.

Whenever a chiral carbon is present in a chemical structure, it is intended that all stereoisomers associated with that chiral carbon are encompassed by the structure.

The invention provides a compound of formula I,

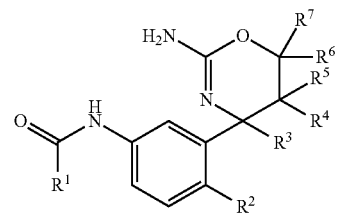

I wherein
$R^1$ is aryl or heteroaryl, each substituted by 1-4 substituents individually selected from halogen-$C_{2-6}$-alkenyl, halogen-$C_{2-6}$-alkynyl, $C_{1-6}$-alkoxy-$C_{2-6}$-alkenyl, $C_{1-6}$-alkoxy-$C_{2-6}$-alkynyl, $C_{2-6}$-alkenyl-$C_{1-6}$-alkoxy and $C_{2-6}$-alkynyl-$C_{1-6}$-alkoxy;
$R^2$ is halogen;
$R^3$ is $C_{1-6}$-alkyl;
$R^4$ is selected from the group consisting of
  i) hydrogen,
  ii) $C_{1-6}$-alkyl, and
  iii) halogen;
$R^5$ is selected from the group consisting of
  i) hydrogen,
  ii) $C_{1-6}$-alkyl, and
  iii) halogen;

$R^6$ is selected from the group consisting of
i) hydrogen, and
ii) $C_{1-6}$-alkyl;
$R^7$ is selected from the group consisting of
i) hydrogen, and
ii) $C_{1-6}$-alkyl;
and when $R^1$ is heteroaryl substituted by $C_{2-6}$-alkynyl-$C_{1-6}$-alkoxy, then $R^4$ and $R^5$ are both hydrogen or are both halogen; or pharmaceutically acceptable salts thereof.

A certain embodiment of the invention provides a compound of formula I as described herein, wherein $R^1$ is heteroaryl substituted by 1-2 substituents individually selected from halogen-$C_{2-6}$-alkenyl, halogen-$C_{2-6}$-alkynyl, $C_{1-6}$-alkoxy-$C_{2-6}$-alkenyl, $C_{1-6}$-alkoxy-$C_{2-6}$-alkynyl, $C_{2-6}$-alkenyl-$C_{1-6}$-alkoxy and $C_{2-6}$-alkynyl-$C_{1-6}$-alkoxy A certain embodiment of the invention provides a compound of formula I as described herein, wherein $R^1$ is heteroaryl substituted by halogen-$C_{2-6}$-alkenyl, halogen-$C_{2-6}$-alkynyl, $C_{1-6}$-alkoxy-$C_{2-6}$-alkenyl, $C_{1-6}$-alkoxy-$C_{2-6}$-alkynyl, $C_{2-6}$-alkenyl-$C_{1-6}$-alkoxy or $C_{2-6}$-alkynyl-$C_{1-6}$-alkoxy.

A certain embodiment of the invention provides a compound of formula I as described herein, wherein $R^1$ is pyrazinyl substituted by halogen-$C_{2-6}$-alkenyl, halogen-$C_{2-6}$-alkynyl, $C_{1-6}$-alkoxy-$C_{2-6}$-alkenyl, $C_{1-6}$-alkoxy-$C_{2-6}$-alkynyl, $C_{2-6}$-alkenyl-$C_{1-6}$-alkoxy or $C_{2-6}$-alkynyl-$C_{1-6}$-alkoxy.

A certain embodiment of the invention provides a compound of formula I as described herein, wherein $R^1$ is $C_{2-6}$-alkynyl-$C_{1-6}$-alkoxy-pyrazinyl.

A certain embodiment of the invention provides a compound of formula I as described herein, wherein $R^1$ is 5-but-2-ynyloxy-pyrazinyl.

A certain embodiment of the invention provides a compound of formula I as described herein, wherein $R^1$ is 5-but-2-ynyloxy-pyrazin-2-yl.

A certain embodiment of the invention provides a compound of formula I as described herein, wherein $R^2$ is F.

A certain embodiment of the invention provides a compound of formula I as described herein, wherein $R^3$ is $C_{1-6}$-alkyl.

A certain embodiment of the invention provides a compound of formula I as described herein, wherein $R^3$ is methyl.

A certain embodiment of the invention provides a compound of formula I as described herein, wherein $R^4$ and $R^5$ are both hydrogen.

A certain embodiment of the invention provides a compound of formula I as described herein, wherein $R^4$ and $R^5$ are both halogen.

A certain embodiment of the invention provides a compound of formula I as described herein, wherein $R^4$ and $R^5$ are both F.

A certain embodiment of the invention provides a compound of formula I as described herein, wherein $R^4$ is hydrogen.

A certain embodiment of the invention provides a compound of formula I as described herein, wherein $R^4$ is halogen.

A certain embodiment of the invention provides a compound of formula I as described herein, wherein $R^4$ is F.

A certain embodiment of the invention provides a compound of formula I as described herein, wherein $R^4$ is $C_{1-6}$-alkyl.

A certain embodiment of the invention provides a compound of formula I as described herein, wherein $R^4$ is methyl.

A certain embodiment of the invention provides a compound of formula I as described herein, wherein $R^5$ is hydrogen.

A certain embodiment of the invention provides a compound of formula I as described herein, wherein $R^5$ is halogen.

A certain embodiment of the invention provides a compound of formula I as described herein, wherein $R^5$ is F.

A certain embodiment of the invention provides a compound of formula I as described herein, wherein $R^5$ is $C_{1-6}$-alkyl.

A certain embodiment of the invention provides a compound of formula I as described herein, wherein $R^5$ is methyl.

A certain embodiment of the invention provides a compound of formula I as described herein, wherein $R^6$ and $R^7$ are both hydrogen.

A certain embodiment of the invention provides a compound of formula I as described herein, wherein $R^6$ is hydrogen.

A certain embodiment of the invention provides a compound of formula I as described herein, wherein $R^6$ is $C_{1-6}$-alkyl.

A certain embodiment of the invention provides a compound of formula I as described herein, wherein $R^6$ is methyl.

A certain embodiment of the invention provides a compound of formula I as described herein, wherein $R^7$ is hydrogen.

A certain embodiment of the invention provides a compound of formula I as described herein, wherein $R^7$ is $C_{1-6}$-alkyl.

A certain embodiment of the invention provides a compound of formula I as described herein, wherein $R^7$ is methyl.

A certain embodiment of the invention provides a compound of formula I as described herein, which is 5-But-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide.

A certain embodiment of the invention provides a compound of formula I as described herein, which is a Tritium labelled compound of formula Ia, wherein $R^1$, $R^2$, $R^3$, $R^4$, $R^5$, $R^6$ and $R^7$ have the meanings as described herein,

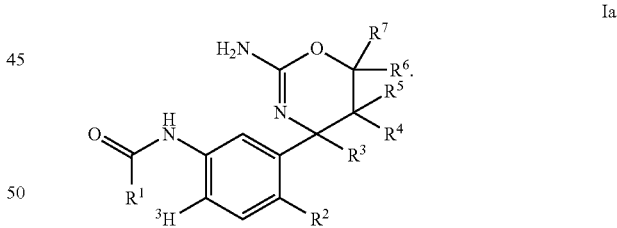

A certain embodiment of the invention provides a compound of formula I as described herein, which is [$^3$H]-5-But-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide.

A certain embodiment of the invention provides a Tritium labelled compound of formula Ia as described herein, which is [$^3$H]-5-But-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide.

A certain embodiment of the invention provides a compound of formula I, which is a $^{11}$C-labelled compound of formula Ia', wherein $R^2$, $R^3$, $R^4$, $R^5$, $R^6$ and $R^7$ have the meanings as described herein,

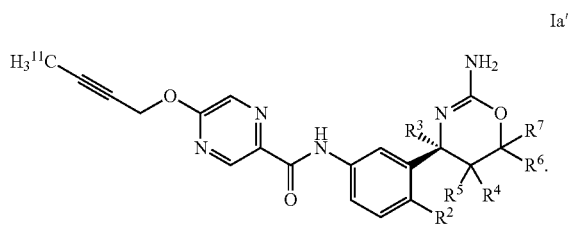

A certain embodiment of the invention provides a $^{11}$C-labelled compound of formula Ia', which is [$^{11}$C]-5-But-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide.

A certain embodiment of the invention provides a $^{11}$C-labelled compound of formula I, which is [$^{11}$C]-5-But-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide.

A certain embodiment of the invention provides a compound of formula I as described herein for use as BACE1 tracer.

A certain embodiment of the invention provides a compound of formula I as described herein for use in a BACE1 binding study.

A certain embodiment of the invention provides a compound of formula I as described herein for use as a PET tracer.

A certain embodiment of the invention provides a compound of formula I as described herein for use in diagnostic imaging of BACE1 in the brain of a mammal.

A certain embodiment of the invention provides a method for diagnostic imaging of the BACE1 enzyme which comprises administering to a mammal an effective amount of a compound as defined herein.

A certain embodiment of the invention provides the use of a compound as defined herein for the manufacture of a composition for diagnostic imaging of BACE1 in the brain of a mammal.

A certain embodiment of the invention provides a compound of formula Ia as described herein for use as BACE1 tracer.

A certain embodiment of the invention provides a compound of formula Ia as described herein for use in a BACE1 binding study.

A certain embodiment of the invention provides a compound of formula Ia as described herein for use as a PET tracer.

A certain embodiment of the invention provides a compound of formula Ia as described herein for use in diagnostic imaging of BACE1 in the brain of a mammal.

A certain embodiment of the invention provides a method for diagnostic imaging of the BACE1 enzyme which comprises administering to a mammal an effective amount of a compound of formula Ia as defined herein.

A certain embodiment of the invention provides the use of a compound of formula Ia as defined herein for the manufacture of a composition for diagnostic imaging of BACE1 in the brain of a mammal.

The invention also provides pharmaceutical compositions, methods of using, and methods of preparing the aforementioned compounds.

A certain embodiment of the invention provides a compound of formula I as described herein for use as therapeutically active substance.

A certain embodiment of the invention provides a compound of formula I as described herein for the use as inhibitor of BACE1 and/or BACE2 activity.

A certain embodiment of the invention provides a compound of formula I as described herein for the use as inhibitor of BACE1 activity.

A certain embodiment of the invention provides a compound of formula I as described herein for the use as inhibitor of BACE2 activity.

A certain embodiment of the invention provides a compound of formula I as described herein for the use as inhibitor of BACE1 and BACE2 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a compound of formula I as described herein for the use as therapeutically active substance for the therapeutic and/or prophylactic treatment of diabetes, particularly type 2 diabetes.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 and/or BACE2 activity.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the use in inhibition of BACE2 activity.

A certain embodiment of the invention provides the use of a compound of formula I as described herein for the manufacture of a medicament for the use in inhibition of BACE1 and BACE2 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes, particularly type 2 diabetes.

A certain embodiment of the invention provides a compound of formula I as described herein for the use in inhibition of BACE1 and/or BACE2 activity.

A certain embodiment of the invention provides a compound of formula I as described herein for the use in inhibition of BACE1 activity.

A certain embodiment of the invention provides a compound of formula I as described herein for the use in inhibition of BACE2 activity.

A certain embodiment of the invention provides a compound of formula I as described herein for the use in inhibition of BACE1 and BACE2 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides a compound of formula I as described herein for the use in the therapeutic and/or prophylactic treatment of Alzheimer's disease.

A certain embodiment of the invention provides a compound of formula I as described herein for the use in the therapeutic and/or prophylactic treatment of diabetes, particularly type 2 diabetes.

A certain embodiment of the invention provides a method for the use in inhibition of BACE1 and/or BACE2 activity, particularly for the therapeutic and/or prophylactic treatment of diseases and disorders characterized by elevated β-amyloid levels and/or β-amyloid oligomers and/or β-amyloid plaques and further deposits, Alzheimer's disease, diabetes or type 2 diabetes, which method comprises administering compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates.

The skilled person in the art will recognize that the compounds of formula I can exist in tautomeric forms, e.g. in the following tautomeric forms:

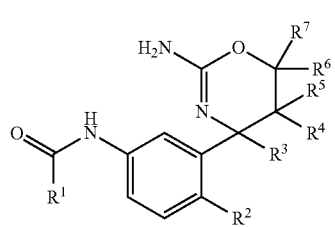

I'

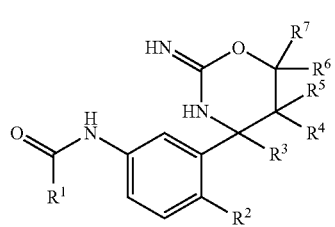

I"

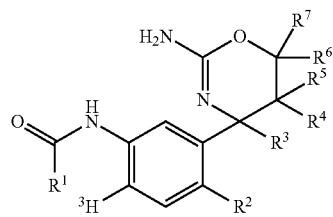

I'a

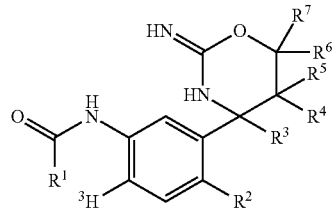

I"a

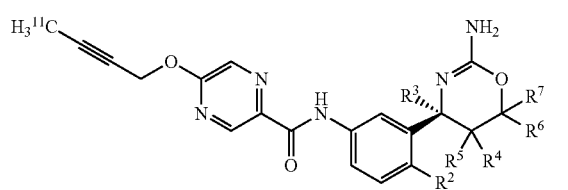

I'a'

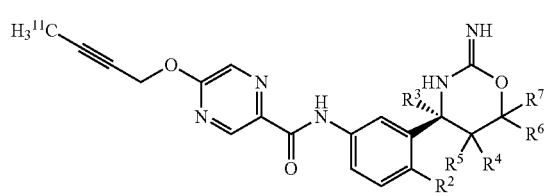

I"a'

All tautomeric forms are encompassed in the present invention.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Particular examples of isomers of a compound of formula I is a compound of formula Ib or a compound of formula Ic, wherein the residues have the meaning as described in any of the embodiments. Particular is compound of formula Ic.

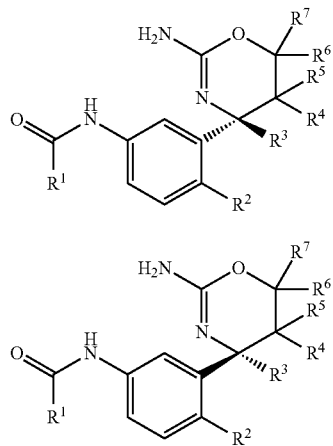

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

The compounds of formula I can be prepared in accordance with the following schemes. The starting material is commercially available or can be prepared in accordance with known methods. Any previously defined residues and variables will continue to have the previously defined meaning unless otherwise indicated.

Sulfinyl imines of general formula A2 can be prepared in analogy to T. P. Tang & J. A. Ellman, J. Org. Chem. 1999, 64, 12, by condensation of an aryl ketone A1 and a sulfinamide, e.g. an alkyl sulfinamide, most particularly (R)-(+)-tert-butylsulfinamide, in the presence of a Lewis acid such as e.g. a titanium(IV)alkoxide, more particularly titanium(IV)ethoxide in a solvent such as an ether, e.g. diethyl ether or more particularly tetrahydrofuran.

The conversion of the sulfinyl imine A2 to the sulfinamide ester A3 proceeds stereoselectively by the chiral directing group as described by Tang & Ellman. The sulfinyl imine A2 can be reacted with a titanium enolate generated from e.g. an alkyl acetate or alkyl 2-halogen-propanoate, particularly ethyl acetate or 2-fluoro-propanoate, lithium diisopropylamide and chlorotriisopropoxytitanium at low temperature, particularly at −78° C. in a solvent such as an ether, e.g. diethyl ether or more particularly tetrahydrofuran. Alternatively sulfinamide ester A3 can be produced from sulfinyl imine A2 by Reformatsky reaction of a bromoacetic ester derivative, particularly ethyl 2-bromo-2-fluoroacetate or 2-bromo-2,2-difluoroacetate, and zinc dust, optionally in the presence of copper(I) chloride, in a solvent such as an ether, e.g. diethyl ether or more particularly tetrahydrofuran, at temperatures from 0 to 70° C., particularly at 23° C.

The alcohol of formula A4 can be prepared by the reduction of an ethylester of formula A3 with an alkali hydride, particularly lithium borohydride or lithium aluminium hydride, in a solvent such as an ether, e.g. diethyl ether or more particularly tetrahydrofuran.

Hydrolysis of the chiral directing group in the sulfinamide alcohol of formula A4 to give the aminoalcohol of formula A5 can be accomplished with a mineral acid, e.g. sulfuric acid or particularly hydrochloric acid, in a solvent such as an ether, e.g. diethyl ether, tetrahydrofuran or more particularly 1,4-dioxane.

The aminooxazine of formula A6 can be prepared by reaction of an aminoalcohol of formula A5 with cyanogen bromide in a solvent such as an alcohol, particularly ethanol.

The nitro derivative of formula A7 can be prepared by nitration of the oxazine A6, wherein Q is hydrogen, following a standard procedure involving neat sulfuric acid and fuming nitric acid without using a solvent.

The reduction of the nitro group in compounds of formula A7 to give anilines of formula A8 can be accomplished by hydrogenation using a catalyst, such as palladium on carbon, in protic solvents, such as alcohols, in particular ethanol or methanol.

Alternatively, the reduction of derivatives of formula A6, wherein Q is a nitro group, to give anilines of formula A8 can be accomplished by hydrogenation using a catalyst, such as palladium on carbon, in protic solvents, such as alcohols, in particular ethanol or methanol.

Target amides of formula I.1 can be prepared by selective coupling of anilines of formula A8 and a carboxylic acid of formula $R^1$—COOH with 4-(4,6-dimethoxy[1.3.5]triazin-2-yl)-4-methylmorpholinium chloride (DMTMM) hydrate as the condensating agent in a solvent such as methanol.

Scheme A: Synthesis of compounds of formula I.1

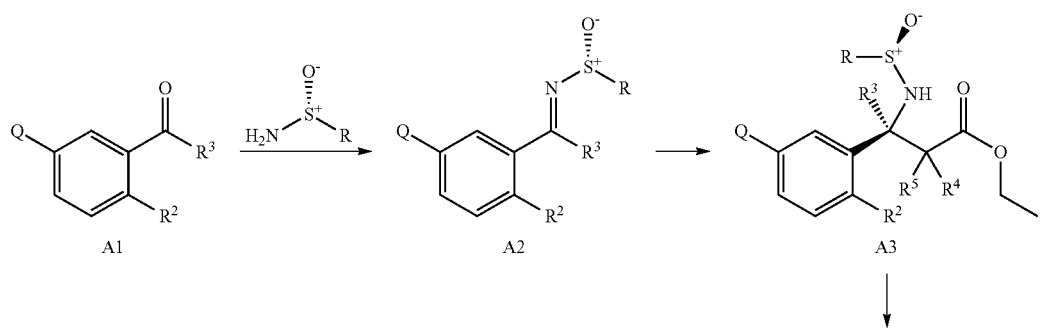

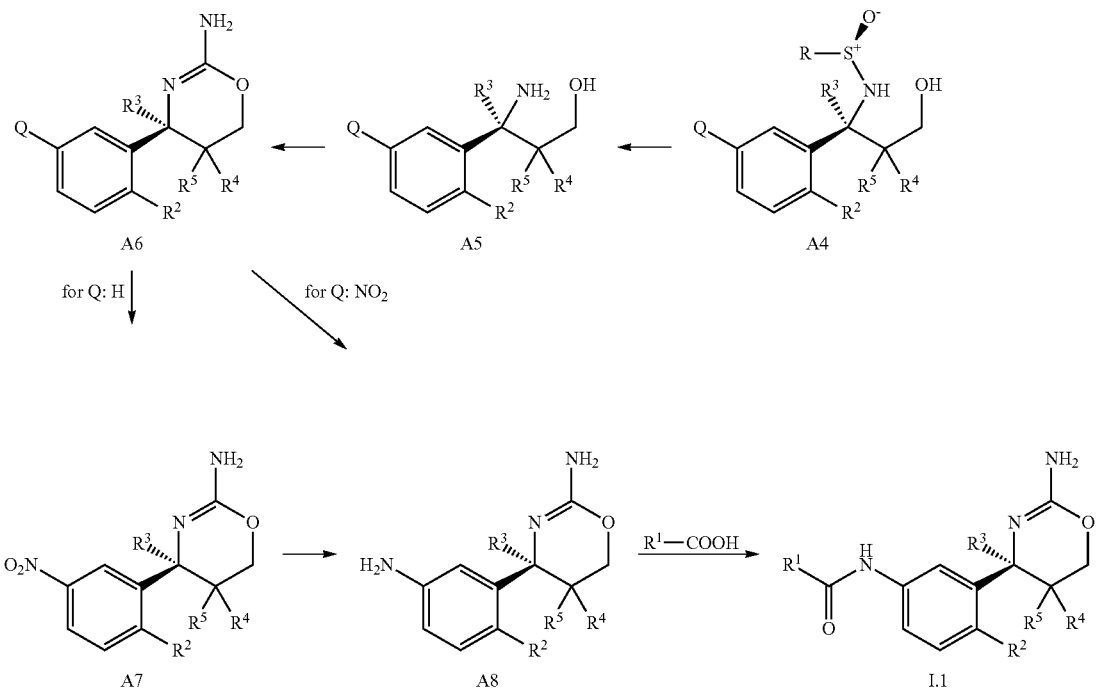

Q: H, Br, NO$_2$
R = C$_{1-6}$-alkyl, preferably t-butyl

Sulfinamide esters of formula A3 can be transformed into alcohols of formula B1 by the reaction of the ethylester with an excess of a Grignard or an organolithium reagent, e.g. methyl- or ethylmagnesium halide, methyllithium etc., in a solvent such as an ether, e.g. diethyl ether or more particularly tetrahydrofuran, at temperatures between −78 and 70° C., particularly at 0 to 23° C.

Hydrolysis of the chiral directing group in the alcohols of formula B1 to give the amino alcohols of formula B2 can be accomplished with a mineral acid, e.g. sulfuric acid or particularly hydrochloric acid in a solvent such as an ether, e.g. diethyl ether or tetrahydrofuran, more particularly 1,4-dioxane, at temperatures from 0 to 23° C.

The aminooxazines of formula B3 can be prepared by reaction of the amino alcohols of formula B2 with cyanogen bromide in a solvent such as an alcohol, particularly ethanol.

The nitro derivative of formula B4 can be prepared by nitration of the oxazine B3, wherein Q is hydrogen, following a standard procedure involving neat sulfuric acid and fuming nitric acid without using a solvent.

The reduction of the nitro group in compounds of formula B4 to give anilines of formula B5 can be accomplished by hydrogenation using a catalyst, such as palladium on carbon, in protic solvents, such as alcohols, in particular ethanol or methanol.

Alternatively, the reduction of derivatives of formula B3, wherein Q is a nitro group, to give anilines of formula B5 can be accomplished by hydrogenation using a catalyst, such as palladium on carbon, in protic solvents, such as alcohols, in particular ethanol or methanol.

Scheme B: Synthesis of intermediate anilines of formula B5.

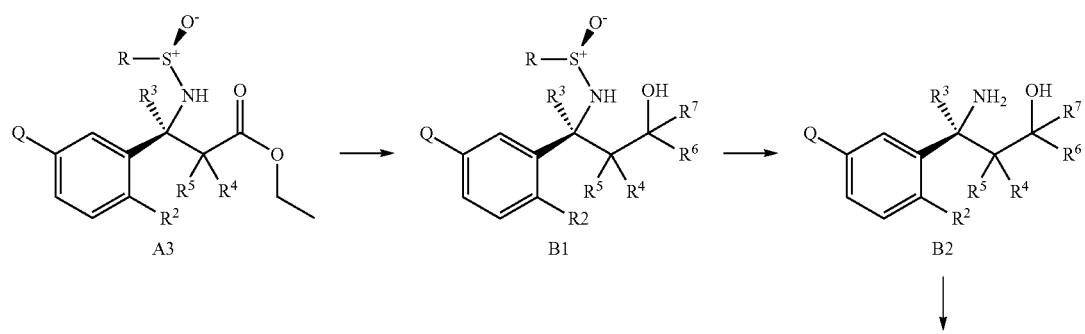

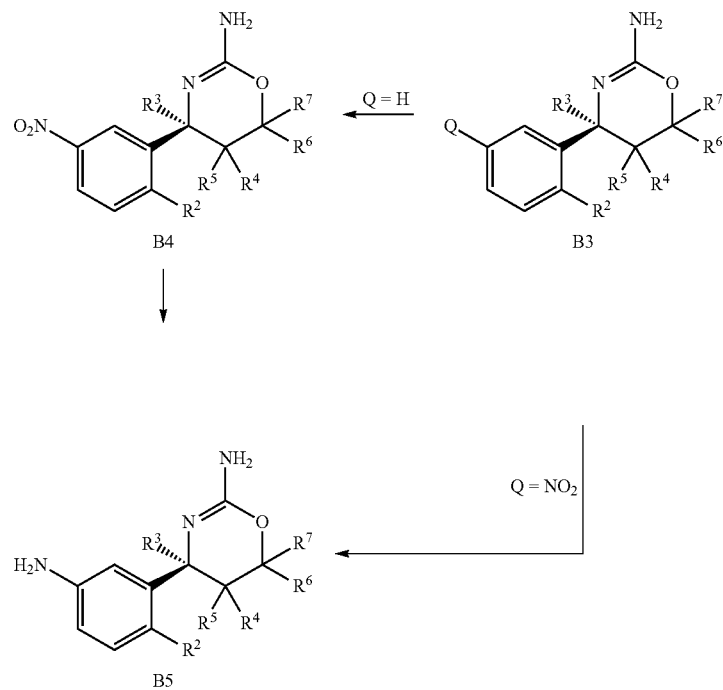

Another typical procedure for the preparation of anilines of formula A8/B5 via N-protected intermediates is illustrated in Scheme A.1.

Protection of the amino group in compounds of formula A6.1, wherein Q is bromine, to produce aryl bromides of formula C1 can be performed with triarylmethyl chlorides, such as triphenylmethyl chloride (Tr-Cl), p-methoxyphenyl-diphenylmethyl chloride (MMTr-Cl), di(p-methoxyphenyl)phenylmethyl chloride (DMTr-Cl) or tri(p-methoxyphenyl)methyl chloride (TMTr-Cl), particularly DMTr-Cl, under basic conditions, e.g. in the presence of an amine, such as triethylamine or diisopropylethylamine, in a chlorinated solvent, such as dichloromethane or chloroform, at temperatures between 0° C. and ambient temperature.

Aryl bromides of formula C1 can be reacted with ammonia equivalents, such as benzophenone imine, in the presence of a suitable transition metal catalyst, such as bis(dibenzylideneacetone)palladium (0) ((dba)$_2$Pd) or tris(dibenzylideneacetone)dipalladium (0) ((dba)$_3$Pd$_2$)), and a suitable ligand, such as rac-2,2'-bis(diphenylphosphino)-1,1'-binaphthyl (rac-BINAP), 2-dicyclohexylphosphino-2',4',6'-triisopropyl-biphenyl (X-PHOS) or 2-di-tert-butylphosphino-2',4',6'-tri-isopropylbiphenyl (t-Bu X-PHOS), in the presence of a base, such as sodium tert-butoxide, potassium phosphate or cesium carbonate, in a suitable solvent, such as toluene or 1,4-dioxane, under an inert atmosphere, such as nitrogen or argon, at temperatures between 80 and 110° C., to produce compounds of formula C2.

Deprotection of both amino groups in compounds of formula C2 can be achieved by a one-pot procedure by first reacting it with a strong organic acid, such as trifluoroacetic acid, in chlorinated solvents, such as dichloromethane or chloroform, under anhydrous conditions at temperatures between 0° C. and ambient temperature to cleave the P$^1$-group. Then the addition of water to cleave the benzophenone imine and reaction at ambient temperature produces diamines of formula A8/B5.

Scheme C: Alternative synthesis of intermediate anilines of formula A8/B5.

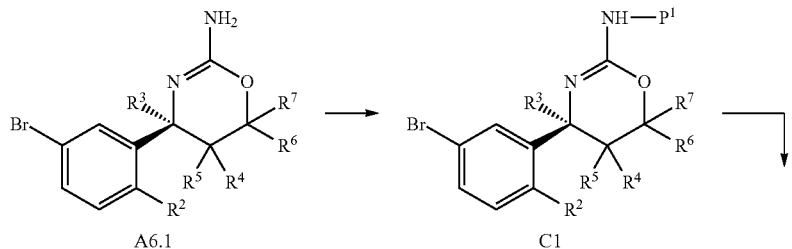

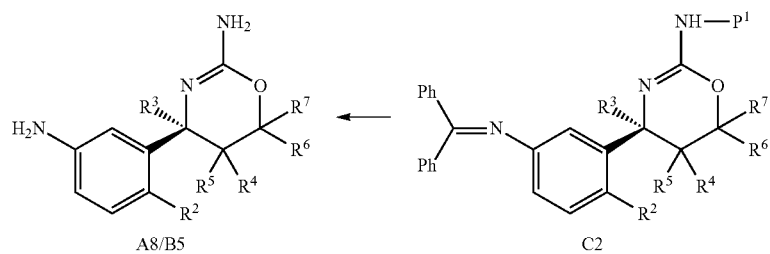

Q = Br
P¹: e.g. Tr, MMTr, DMTr, TMTr

Anilines of formula A8/B5, can be transformed to iodo derivatives of formula D1 by iodonium donating systems using iodides as an iodide source, like e.g. ammonium iodide, together with a strong oxidizing agent, like e.g. hydrogen peroxide, in a polar solvent, like e.g. acetic acid, and as described by N. Narender et al. in Tetrahedron Letters 48 (2007) 6124-6128.

Intermediate tritiated amines of formula D2 can be accomplished by procedures known to those skilled in the art. Treatment of iodo derivatives of formula D1 with tritium gas in inert solvents, like e.g. ethyl acetate, in presence of palladium as the catalyst yields tritium labelled compounds of formula D2.

Target amides of formula Ia can be prepared by selective coupling of tritiated anilines of formula D2 and a carboxylic acid of formula $R^1$—COOH with 4-(4,6-dimethoxy[1.3.5]triazin-2-yl)-4-methylmorpholinium chloride (DMTMM) hydrate as the condensating agent in a solvent such as methanol.

tive coupling in the presence of 4-(4,6-dimethoxy[1.3.5]triazin-2-yl)-4-methylmorpholinium chloride (DMTMM) hydrate as the condensating agent in a solvent such as methanol.

Protection of the amino group in compounds of formula D1 to produce carbamates of formula D2 can be performed with a reagent such as $Boc_2O$ in a solvent such as dichlorometane.

Intermediates of formula D2 can be transformed in propargyl ethers of formula D3 by reaction with propargyl alcohol in the presence of a base such as KOtBu in a solvent such as DMF.

The protecting group on compounds of formula D3 can be removed to obtain intermediates D4 by treatment with an appropriate acid, such as for example TFA, in a solvent such as DCM.

A terminal acetylene of the structure D4 can be stannylated to obtain a compound of formula D5. Appropriate conditions for such a transformation are for example the use of tri-n-butyltinmethoxide and heating of the reaction mixture.

Scheme D: Synthesis of intermediate anilines of formula D2.

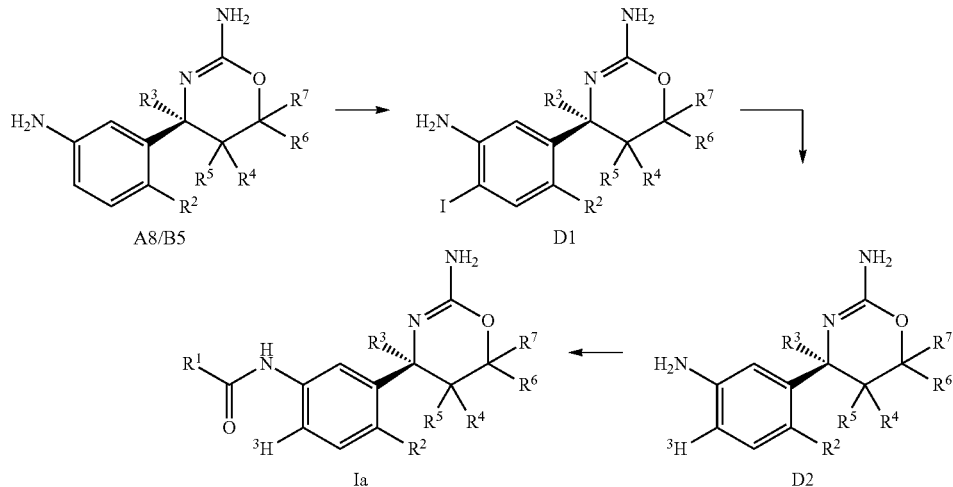

Target amides of formula Ia' can be prepared by from intermediates A8/B5 as depicted in Scheme E. The intermediates A8/B5 can be converted in amides of formula D1 by reaction with 5-chloropyrazine-2-carboxylic acid by selec-

[$^{11}$C]-Labeled compounds of formula Ia' can be obtained by palladium catalyzed (e.g. [Pd(tBu$_3$)$_2$]) coupling of tributylstannyl acetylenes of formula D5 and [$^{11}$C]methyl iodide in a solvent such as DMF.

Scheme E: Synthesis of [¹¹C] methyl acetylenes of formula Ia'
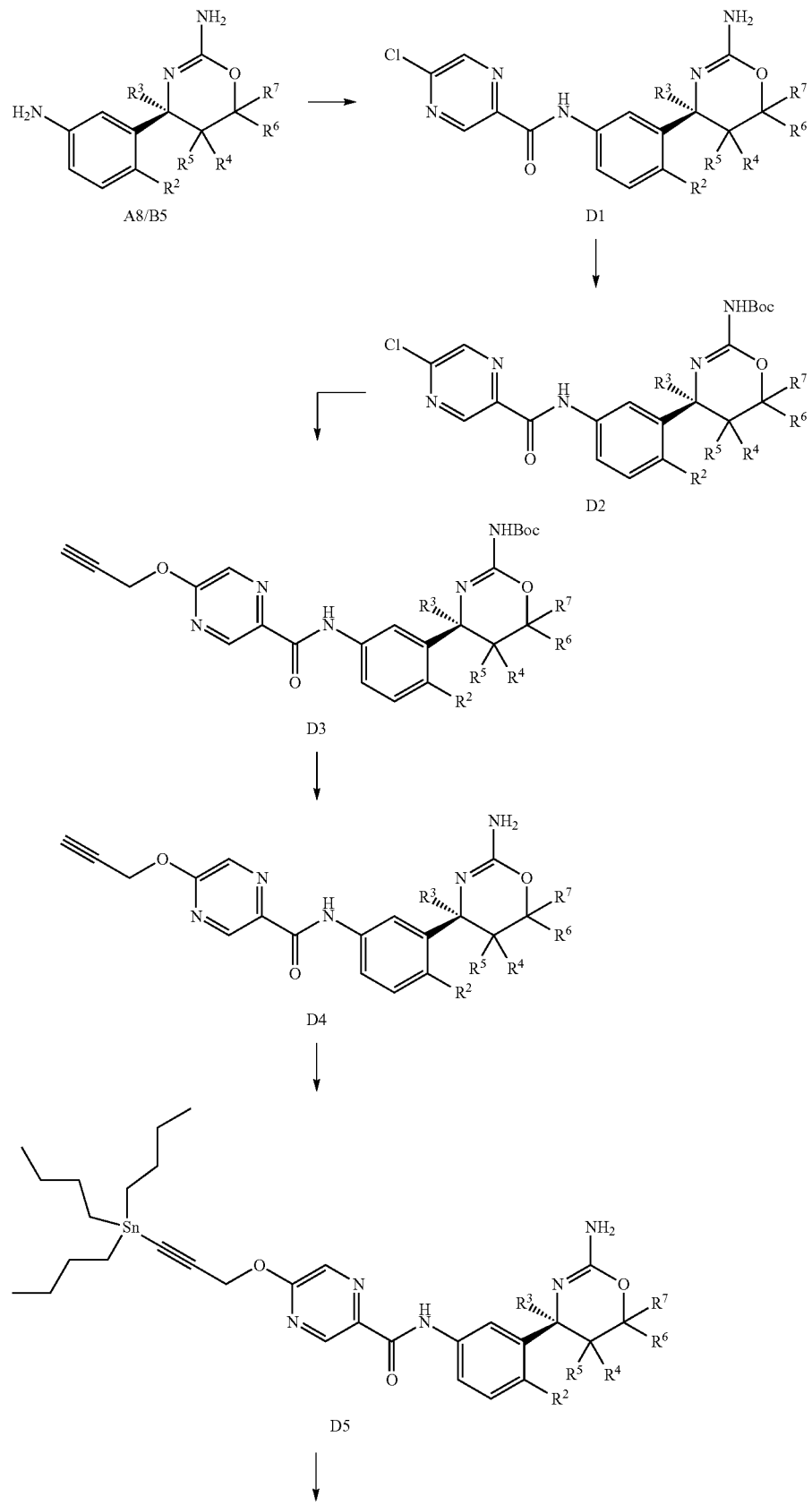

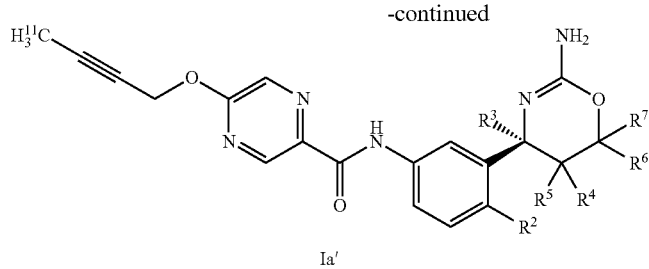

Ia'

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the compounds of formula I as well as all intermediate products can be prepared according to analogous methods or according to the methods set forth herewithin. Starting materials are commercially available, known in the art or can be prepared by methods known in the art or in analogy thereto.

It will be appreciated that the compounds of general formula I in this invention can be derivatised at functional groups to provide derivatives which are capable of conversion back to the parent compound in vivo.

Pharmacological Tests

The compounds of formula I and their pharmaceutically acceptable salts possess valuable pharmacological properties. It has been found that the compounds of the present invention are associated with inhibition of BACE1 and/or BACE2 activity. The compounds were investigated in accordance with the test given hereinafter.

Cellular Aβ-Lowering Assay:

a) Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96 well ELISA plates (e.g., Nunc MaxiSorb) were coated with monoclonal antibody which specifically recognize the C-terminal end of Aβ40 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/ $H_2O_2$ in citric acid buffer. After stopping the reaction with one volume 1 N $H_2SO_4$ the reaction was measured in an ELISA reader at 450 nm wavelength. The concentrations of Aβ in the culture supernatants were calculated from a standard curve obtained with known amounts of pure Aβ peptide.

b) Alternatively, the Abeta 40 AlphaLISA Assay can be used. The HEK293 APP cells were seeded in 96 well Microtiter plates in cell culture medium (Iscove's, plus 10% (v/v) fetal bovine serum, penicillin/streptomycin) to about 80% confluency and the compounds were added at a 3× concentration in 1/3 volume of culture medium (final DMSO concentration was kept at 1% v/v). After 18-20 hrs incubation at 37° C. and 5% $CO_2$ in a humidified incubator, the culture supernatants were harvested for the determination of Aβ40 concentrations using Perkin-Elmer Human Amyloid beta 1-40 (high specificity) Kit (Cat# AL275C).

In a Perkin-Elmer White Optiplate-384 (Cat#6007290), 2 μl culture supernatants were combined with 2 μl of a 10× AlphaLISA Anti-hAβAcceptor beads+Biotinylated Antibody Anti-Aβ 1-40 Mix (50 μg/mL/5 nM). After 1 hour room temperature incubation, 16 μl of a 1.25× preparation of Streptavidin (SA) Donor beads (25 μg/mL) were added and incubated for 30 minutes in the Dark. Light Emission at 615 nm was then recorded using EnVision-Alpha Reader. Levels of Aβ40 in the culture supernatants were calculated as percentage of maximum signal (cells treated with 1% DMSO without inhibitor). The IC50 values were calculated using the Excel XLfit software.

Assay for BACE Inhibition by Measuring Cellular TMEM27 Cleavage:

The assay uses the principle of inhibition of human TMEM27 cleavage by endogenous cellular BACE2 in the Ins1e rat cell line and shedding from the cell surface into the culture medium, followed by detection in an ELISA assay. Inhibition of BACE2 prevents the cleavage and shedding in a dose-dependent manner.

The stable cell line "INS-TMEM27" represents an INS1e-derived cell line with inducible expression (using the TetOn system) of full-length hTMEM27 in a doxycycline-dependent manner. The cells are cultured throughout the experiment in RPMI1640+Glutamax (Invitrogen) Penicillin/Streptomycin, 10% Fetal bovine serum, 100 mM pyruvate, 5 mM beta-mercaptoethanol, 100 micrograms/ml G418 and 100 microgram/ml hygromycin and are grown inadherent culture at 37° C. in a standard $CO_2$ cell culture incubator.

INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An $EC_{50}$ for BACE2 inhibition is calculated using the ELISA readout for each inhibitor concentration with standard curve-fitting software such as XLFit for the Excel spreadsheet program.

For example, an $IC_{50}$ value of 1.1 nM was obtained for 5-But-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide (BACE1 cell act. Aβ40).

Autoradiography Studies with [$^3$H]-5-but-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide (Example 2) in Rat Brains 1) In Vitro Autoradiography The distribution of [$^3$H]-5-but-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide binding sites as well as the binding specificity for BACE1 was investigated by in vitro autoradiography using male Sprague-Dawley rats. Animals were sacrificed, their brains were rapidly removed and frozen in dry ice powder. Ten μm-thick sagittal sections were cut in a Cryostat microtome and thaw-mounted on adhesion glass slides. Brain sections were first incubated for 10 min in Ringer buffer (NaCl 120 mM, KCl 5 mM, $CaCl_2$ 2 mM, $MgCl_2$ 1 mM, Tris-HCl 50 mM pH 7.4) at RT and then for 60 min in Ringer buffer containing either 1 nM or 10 nM [$^3$H]-5-but-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide. For the evaluation of non-specific-binding (NSB) of the radiotracer an additional series of sections was incubated with Ringer buffer containing the radiotracer and a reference BACE1 inhibitor ((S)-3-(3,6-dihydro-2H-pyran-4-yl)-7-(2-fluoropyridin-3-yl)-5'H-spiro[chromeno[2,3-c]pyridine-5,5'-oxazol]-2'-amine, CAS Nr 1215869-02-5; example 294 in WO2010030954) at 10 μM. At the end of the incubation, sections were rinsed 3×5 min in ice-cold Ringer buffer and then rapidly dipped once in distilled water at 4° C. Slide-mounted brain sections were dried under a flow of cold air for 3 h and exposed together with [$^3$H]-microscale to a Fuji Imaging plate for 5 days. The imaging plate was then scanned in a high resolution Fuji BAS reader. The total amount of radiotracer bound to the brain areas of interest (TB) was measured using the MCID image analysis program and expressed as fmol of bound radiotracer/mg of protein. The amount of [$^3$H]-5-but-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide specifically bound to BACE1 (SB) was calculated according to the formula SB=TB−NSB. The results obtained showed a widespread distribution of example 2 binding sites in the rat brain which is in line with the known distribution of BACE1 mRNA (Brian D. Bennett, Safura Babu-Khan, Richard Loeloff, Jean-Claude Louis, Eileen Curran, Martin Citron, and Robert Vassar, The Journal of Biological Chemistry. 275, 20647-51, 2000). Highest densities of example 2 binding sites were observed in the dentate gyms and the CA3 region of the hippocampus, the cerebellum, pallidum and substantia nigra. Co-incubation of 1 nM example 2 with 10 μM of the specific BACE1 inhibitor A reduced tracer binding by more than 80% demonstrating that example 2 binds specifically to BACE1 in vitro. Furthermore, the tritiated tracer candidate was used to study and compare binding to BACE1 in brain tissue slices of monkeys and humans by in vitro autoradiography. It could be demonstrated that example 2 binds to BACE1 in a very similar degree, suggesting the translatability of example 2 as a BACE1-specific tracer in various species.

2) Ex Vivo Autoradiography

The in vivo characteristics of [$^3$H]-5-but-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide for imaging BACE1 were analyzed by an ex vivo autoradiographical approach using young male Sprague-Dawley rats. Animals were intravenously injected with 1 mCi/kg [$^3$H]-5-but-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide corresponding to 37.7 nmol/kg and sacrificed at various time points post injection. To test the specificity of tracer binding in vivo, rats were pre-administered with 10 mg/kg of a reference BACE1 inhibitor ((S)-3-(3,6-dihydro-2H-pyran-4-yl)-7-(2-fluoropyridin-3-yl)-5'H-spiro[chromeno[2,3-c]pyridine-5,5'-oxazol]-2'-amine, CAS Nr 1215869-02-5; example 294 in WO2010030954) (p.o.) 3 h prior to tracer injection. Animals were sacrificed at various time points post injection (5, 15, 30, 60, 120 min p.i.), their brains were rapidly removed and frozen in dry ice powder. Ten μm-thick sagittal sections were cut in a Cryostat microtome and thaw-mounted on adhesion glass slides. Slide-mounted brain sections were dried under a flow of cold air for 3 h and exposed together with [$^3$H]-microscale to a Fuji Imaging plate for 5 days. The imaging plate was then scanned in a high resolution Fuji BAS reader. The total amount of radiotracer bound to the brain areas of interest (TB) was measured using the MCID image analysis program and expressed as fmol of bound radiotracer/mg of protein. The amount of [$^3$H]-5-but-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide specifically bound to BACE1 (SB) was calculated according to the formula SB=TB−NSB. [$^3$H]-5-But-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide was found to enter the rat brain showing favorable brain over plasma ratios. The observed distribution pattern of in vivo binding perfectly corresponded to the in vitro distribution with highest accumulation in the dentate gyms and the CA3 region of the hippocampus, the cerebellum, pallidum and substantia nigra. In addition, in vivo accumulation of example 2 was found to be mainly BACE1-specific since binding was clearly reduced by pre-treatment with the BACE1 ligand A. Analysis of tracer binding at various time points post injection demonstrated favorable wash-out kinetics of example 2 binding during a typical PET acquisition time of 120 min.

In vivo PET Imaging with [$^{11}$C]-5-but-2-ynyloxy-pyrazine-2-carboxylic acid[3-((R)-2-amino-5,5-difluoro-4-methyl-5,6-dihydro-4H-[1,3]oxazin-4-yl)-4-fluoro-phenyl]-amide in the Baboon The PET experiments were carried out in male baboons (papio anubis). Animals were fasted for 12 hours prior to the PET study. Baboons were initially sedated intramuscularly with Ketamine hydrochloride with restraint dosages of 5-7 mg/kg to achieve a superficial level of anesthesia and then maintained on continuous Propofol intravenous infusion @ 0.3-0.4 mg/kg/h (DIPRIVAN® Injectable Emulsion). Circulatory volume was maintained by infusion of isotonic saline. A femoral arterial catheter was inserted for blood sampling. Physiological vital signs including heart rate, ECG, blood pressure and oxygen saturation were continuously monitored throughout the study. The animal was positioned in an ECAT HRRT® brain PET scanner (High Resolution Research Tomograph, CPS Innovations, Inc., Knoxville, Tenn.). The head of the animal was fitted with a thermoplastic mask that was attached to a head holder for reproducible fixation. A 6 min transmission scan with a 1 mCi Cs-137 point source was initially done for attenuation correction. [$^{11}$C]-5-But-2-ynyloxy-pyrazine-2-carboxylic acid [3-((R)-2-amino-5,5-difluoro-4-methyl-5,6-dihydro-4H-[1,3]oxazin-4-yl)-4-fluorophenyl]-amide (approximately 10 mCi or 1 µg) was administered intravenously as a 1 minute bolus injection. PET scanning and arterial blood sampling was initiated upon start of the radiotracer administration and PET images were acquired from 0 to 120 minutes following administration of the radiotracer. Emission PET scans were reconstructed using the iterative ordered-subset expectation-maximization (OSEM) algorithm correcting for attenuation, scatter, and dead-time. A standard VOI template was transferred to each individual animal's baseline PET. Time-activity curves (TACs) of regions were obtained by applying the VOIs on successive PET frames. The radioactivity of a VOI at time T was calculated as the weighted mean and expressed in mCi/ml. TACs were also expressed by standardized uptake values (SUV) using the following formula to allow rough comparisons of TACs between scans and between scans of different tracers:

SUV (%)=radioactivity (nCi/ml)/106/(dose (mCi)/body weight (kg)×103)×100, where numbers were used to make the unit for radioactivity equivalent between voxel radioactivity and radioactivity dose (106) and between body weight and voxel volume (103).

The results of the PET imaging studies showed that the radiotracer was rapidly taken up in multiple brain areas with TACs that demonstrated peak uptake 10-20 min after administration and a slow decline over the remainder of the study. The ubiquitous distribution of the radiotracer reflected the known distribution of BACE1 (B. D. Bennett et al., *J. Biol Chem.* 2000, 275 (27), 20647-20651) with slightly higher accumulation in the dentate gyms of the hippocampus, globus pallidum and substantia nigra.

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

EXAMPLE A

Tablets of the following composition are manufactured in the usual manner:

TABLE 1 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.

2. Dry the granules at 50° C.

3. Pass the granules through suitable milling equipment.

4. Add ingredient 5 and mix for three minutes; compress on a suitable press.

EXAMPLE B-1

Capsules of the following composition are manufactured:

TABLE 2 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

EXAMPLE B-2

Soft Gelatin Capsules of the following composition are manufactured:

TABLE 3 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 4 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 5 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

EXAMPLE D

Injection solutions of the following composition are manufactured:

TABLE 6 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 7 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

Synthesis of the Intermediate Sulfinyl Imines A2

General Procedure:

A solution of the (R)-(+)-tert-butylsulfinamide (89.8 mmol) in tetrahydrofuran (400 ml) was treated subsequently with the ketone (98.7 mmol) and titanium(IV)ethoxide (178.4 mmol). The solution was stirred at reflux temperature for 3 to 18 hours. For the workup, the mixture was cooled to 22° C. and treated with brine (400 ml). The suspension was stirred for 10 minutes and filtered over dicalite. The layers were separated, the aqueous layer was extracted with ethyl acetate, the combined organic layers were washed with water, dried and evaporated. The residue was purified by chromatography on silica using a mixture of heptane and ethyl acetate as eluent to give the pure sulfinyl imines A2.

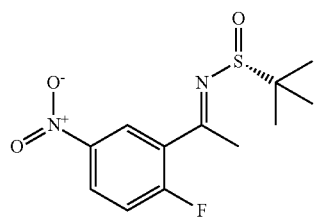 [SMILES: C/C(=N\[S@](=O)C(C)(C)C)c1cc([N+](=O)[O-])ccc1F]

Intermediate A2.1 (Q=$NO_2$; $R^2$=F; $R^3$=Me): Starting from 1-(2-fluoro-5-nitro-phenyl)-ethanone (89.7 mmol), the product (R)-2-methyl-propane-2-sulfinic acid [1-(2-fluoro-5-nitro-phenyl)-(E)-ethylidene]-amide (21.56 g) was obtained as a pale yellow solid. MS (ISP): m/z=287.0 [M+H]$^+$.

Synthesis of the Intermediate Sulfinamide Difluoroesters A3

General Procedure (Via Reformatsky Reaction):

In a dry apparatus a suspension of freshly activated zinc powder (1.28 g, 19.6 mmol) in dry diethyl ether (45 ml) was heated under an inert atmosphere to reflux. A solution of the sulfinyl imine A2 (9.81 mmol) and ethyl 2-bromo-2,2-difluoroacetate (3.98 g, 2.52 ml, 19.6 mmol) in dry diethyl ether (25 ml) was added dropwise over a period of 15 minutes while the internal temperature rose and reflux increased. The suspension was held at reflux for further 5 hours. For the workup, it was cooled to 23° C., filtered through celite and washed with ethyl acetate. The filtrate was poured into a saturated solution of ammonium chloride (300 ml) and extracted with ethyl acetate (2×300 ml). The combined organic layers were dried over sodium sulphate and evaporated to give 4.59 g crude product as brown oil, which was purified by flash chromatography (silica gel, 70 g) with a 8:1-mixture of heptane and ethyl acetate to give the sulfinamide difluoroesters A3.

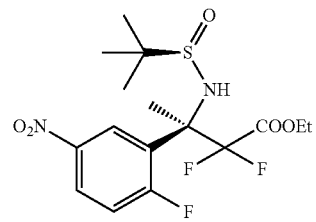 [SMILES: CCOC(=O)C(F)(F)[C@](C)(N[S@](=O)C(C)(C)C)c1cc([N+](=O)[O-])ccc1F]

Intermediate A3.1 (Q=$NO_2$; $R^2$=F; $R^3$=Me; $R^4$=F; $R^5$=F): Starting from (R)-2-methyl-propane-2-sulfuric acid [1-(2-fluoro-5-nitro-phenyl)-(E)-ethylidene]-amide (intermediate A2.1) (5.73 g, 20 mmol), the product (R)-2,2-difluoro-3-(2-fluoro-5-nitro-phenyl)-3-((R)-2-methyl-propane-2-sulfinylamino)-butyric acid ethyl ester (3.1 g) was obtained as an orange oil. MS (ISP): m/z=411.2 [M+H]$^+$.

Synthesis of the Intermediate Sulfinamide Alcohols A4

A solution of the sulfinamide difluoroesters A3 (4.4 mmol) in dry tetrahydrofuran (24 ml) was cooled to 0° C. and treated with lithium borohydride (9.0 mmol). Stirring was continued at 0° C. for 15 minutes. The reaction mixture was then let to warm up to room temperature and stirred for additional 2 to 18 hours. For the workup, the reaction was quenched by addition of water, the reaction volume was reduced at reduced pressure and diluted with ethyl acetate. The organic phase was washed with brine, dried over sodium sulphate and evaporated to give a residue which was purified by chromatography on silica gel using a mixture of n-heptane and ethyl acetate as the eluent to give the intermediate alcohols A4.

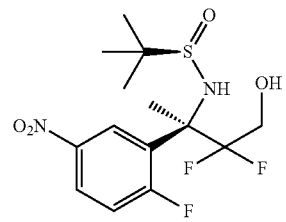 [SMILES: CC(C)(C)[S@@](=O)N[C@](C)(c1cc([N+](=O)[O-])ccc1F)C(F)(F)CO]

Intermediate A4.1 (Q=$NO_2$; $R^2$=F; $R^3$=Me; $R^4$=F; $R^5$=F; $R^6$=H; $R^7$=H): Starting from (R)-2,2-difluoro-3-(2-fluoro-5-nitro-phenyl)-3-((R)-2-methyl-propane-2-sulfinylamino)-butyric acid ethyl ester (intermediate A3.1) (3.78 g, 9.2 mmol), the product (R)-2-methyl-propane-2-sulfinic acid [(R)-2,2-difluoro-1-(2-fluoro-5-nitro-phenyl)-3-hydroxy-1-methyl-propyl]-amide (2.9 g) was obtained as a light yellow solid. MS (ISP): m/z=369.0 [M+H]$^+$.

Synthesis of the Intermediate Amino Alcohols A5

General Procedure:

A solution of the sulfinamide alcohols A4 (10.3 mmol) in methanol or tetrahydrofuran (30 to 60 ml) was treated with a solution of hydrochloric acid (4 M in 1,4-dioxane, 10-13 ml). Stirring was continued at 23° C. for 2 to 18 hours. Thereafter, the mixture was partitioned between ethyl acetate and an aqueous solution of sodium carbonate (2 M). The organic layer was dried over sodium sulphate, filtered and evaporated to give a residue which was purified by chromatography on silica gel using a mixture of n-heptane and ethyl acetate as the eluent to give the pure aminoalcohols A5.

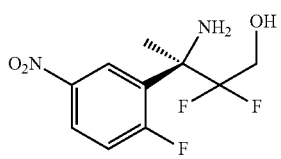 [SMILES: C[C@@](N)(c1cc([N+](=O)[O-])ccc1F)C(F)(F)CO]

Intermediate A5.1 (Q=NO$_2$; R$^2$=F; R$^3$=Me; R$^4$=F; R$^5$=F; R$^6$=H; R$^7$=H): Starting from (R)-2-methyl-propane-2-sulfinic acid [(R)-2,2-difluoro-1-(2-fluoro-5-nitro-phenyl)-3-hydroxy-1-methyl-propyl]-amide (intermediate A4.1) (3.79 g, 10.3 mmol), the product (R)-3-amino-2,2-difluoro-3-(2-fluoro-5-nitro-phenyl)-butan-1-ol (2.5 g) was obtained as a light yellow solid. MS (ISP): m/z=265.1 [M+H]$^+$.

Synthesis of the Intermediate Amino Oxazines A6

General Procedure:

A solution of the amino alcohols A5 (8.4 mmol) in ethanol (40 ml) was treated under argon at 23° C. with cyanogen bromide (1.33 g, 12.6 mmol). The light yellow reaction solution was stirred in a sealed tube for 24 hours at 85° C. Cooled to 23° C., some ice was added to the reaction mixture, followed by extraction with dichloromethane, water, and a saturated solution of sodium hydrogencarbonate (pH=8). The organic layer was dried over sodium sulphate, filtered and evaporated to give the crude product, which was either used in the next step without further purification or purified by chromatography on silica gel using a mixture of n-heptane and ethyl acetate as the eluent to afford the pure amino oxazine A6.

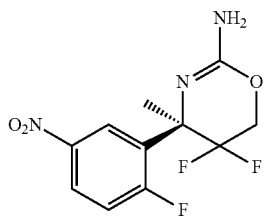 [SMILES: C[C@]1(c2cc([N+](=O)[O-])ccc2F)N=C(N)OCC1(F)F]

Intermediate A6.1 (Q=NO$_2$; R$^2$=F; R$^3$=Me; R$^4$=F; R$^5$=F; R$^6$=H; R$^7$=H): Starting from (R)-3-amino-2,2-difluoro-3-(2-fluoro-5-nitro-phenyl)-butan-1-ol (intermediate A5.1) (1.5 g, 5.7 mmol), the product (R)-5,5-difluoro-4-(2-fluoro-5-nitro-phenyl)-4-methyl-5,6-dihydro-4H-[1,3]oxazin-2-ylamine (1.3 g) was obtained as a light yellow solid. MS (ISP): m/z=290.2 [M+H]$^+$.

Synthesis of the Intermediate Diamines A8 (from Nitro Compounds A6)

General Procedure:

A solution of the nitro compound A6 (4.47 mmol) in ethanol (35 ml) was treated at 23° C. under an inert atmosphere with palladium on carbon (10% Pd/C, 238 mg, 5 mol %) and the mixture was stirred under hydrogen atmosphere (balloon) at 23° C. for 1 hour. The catalyst was filtered off and washed twice with ethanol. The solvent was removed at reduced pressure to give the intermediate diamine A8 as a crude product which was used without further purification.

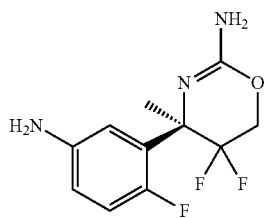 [SMILES: C[C@]1(c2cc(N)ccc2F)N=C(N)OCC1(F)F]

Intermediate A8.1 (R$^2$=F; R$^3$=Me; R$^4$=F; R$^5$=F; R$^6$=H; R$^7$=H): Starting from (R)-5,5-difluoro-4-(2-fluoro-5-nitro-phenyl)-4-methyl-5,6-dihydro-4H-[1,3]oxazin-2-ylamine (intermediate A6.1) (1.29 g, 4.47 mmol), the product (R)-4-(5-amino-2-fluoro-phenyl)-5,5-difluoro-4-methyl-5,6-dihydro-4H-[1,3]oxazin-2-ylamine (1.14 g) was obtained as a colorless foam. MS (ISP): m/z=260.1 [M+H]$^+$.

Synthesis of the Intermediate Iodo Derivatives D1

General Procedure:

A solution of the diamine A8 (500 mg, 1.9 mmol) and ammonium iodide (308 mg, 2.1 mmol) in acetic acid (9.6 ml) was treated at room temperature with an aqueous solution of hydrogen peroxide (35%, 0.19 ml, 2.1 mmol). After stirring overnight 50% of the starting material was left. Another equivalent of ammonium iodide and hydrogen peroxide was added and stirring continued at room temperature overnight. For the workup, the reaction mixture was filtered, the filtrate treated with sodium thiosulphate, then extracted with ethyl acetate (3×). The combined organic layers were washed with a saturated solution of sodium hydrogencarbonate, then dried over sodium sulphate and evaporated at reduced pressure. In order to eliminate residual acetic acid, the crude product was dissolved in dichloromethane and extracted again with a saturated solution of sodium hydrogencarbonate. The crude product was purified by chromatography on an Isolute flash NH$_2$ column using a gradient of heptane/ethyl acetate as the eluent to afford the pure iodo derivative D1.

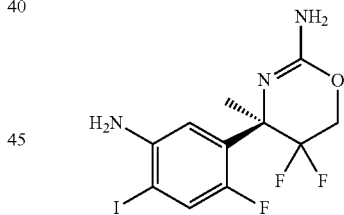

Intermediate D1 (R$^2$=F; R$^3$=Me; R$^4$=F; R$^5$=F; R$^6$=H; R$^7$=H): Starting from (R)-4-(5-amino-2-fluoro-phenyl)-5,5-difluoro-4-methyl-5,6-dihydro-4H-[1,3]oxazin-2-ylamine (intermediate A8.1) (500 mg, 1.9 mmol), the product (R)-4-(5-amino-2-fluoro-4-iodo-phenyl)-5,5-difluoro-4-methyl-5,6-dihydro-4H-[1,3]oxazin-2-ylamine (415 mg) was obtained as a yellow solid. MS (ISP): m/z=386.0 [M+H]$^+$.

Synthesis of the Intermediate Tritium Labelled Amines D2

General Procedure:

In a 2 ml tritiation flask, a mixture of iodo diamine D1 (0.026 mmol), palladium (10% on carbon) (27.6 mg, 0.026 mmol), and triethylamine (7.26 µl, 0.52 mmol) was suspended in ethyl acetate (1.0 ml). The flask was attached to the tritium manifold (RC-TRITEC) and degassed by freeze-pump-thaw. Tritium gas was introduced, and the reaction mixture was vigorously stirred for 4 hours in an atmosphere of tritium at 710 mbar. The mixture was cooled by liquid nitrogen and the excess tritium gas in the reaction vessel was reabsorbed on a uranium-trap for waste-tritium. The solvent was lyophilized off and labile tritium was removed by lyophilization with a 9:1-mixture of ethanol and water (3×1 ml). The remaining black solid was suspended in ethanol (1 ml), filtered over a 0.25 μm syringe filter and washed with ethanol. D2 was collected and stored as a 20 ml ethanolic stock solution.

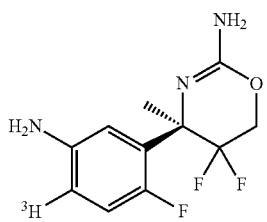 [SMILES: [3H]c1cc(F)c([C@@]2(C)N=C(N)OCC2(F)F)cc1N]

Intermediate D2 ($R^2$=F; $R^3$=Me; $R^4$=F; $R^5$=F; $R^6$=H; $R^7$=H): Starting from (R)-4-(5-amino-2-fluoro-4-iodo-phenyl)-5,5-difluoro-4-methyl-5,6-dihydro-4H-[1,3]oxazin-2-ylamine (intermediate D1) (10 mg, 0.026 mmol), the product [$^3$H]-(R)-4-(5-amino-2-fluoro-phenyl)-5,5-difluoro-4-methyl-5,6-dihydro-4H-[1,3]oxazin-2-ylamine (23.2 GBq, 627 mCi) was obtained. Radio-HPLC analysis indicated a radiochemical purity of 74%. The intermediate was used without further purification.

EXAMPLE 1

5-But-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide

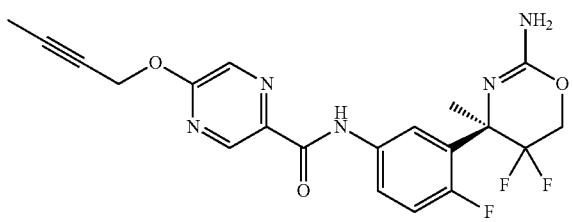 [SMILES: CC#CCOc1cnc(C(=O)Nc2ccc(F)c([C@@]3(C)N=C(N)OCC3(F)F)c2)cn1]

A solution of 4-(4,6-dimethoxy[1.3.5]triazin-2-yl)-4-methylmorpholinium chloride hydrate (DMTMM) (74 mg, 0.25 mmol) in methanol (5 ml) was cooled to 0° C. and treated with 5-(but-2-ynyloxy)pyrazine-2-carboxylic acid (CAS [1221447-98-8]) (40.8 mg, 0.21 mmol). The suspension was stirred at 0° C. for 30 minutes, then a solution of (R)-4-(5-amino-2-fluoro-phenyl)-5,5-difluoro-4-methyl-5,6-dihydro-4H-[1,3]oxazin-2-ylamine (intermediate A8.1) (50 mg, 0.19 mmol) in methanol (1 ml) was added dropwise. The resulting yellow solution was stirred at 0° C. for 4 hours. For the workup, the reaction mixture was evaporated at reduced pressure and the residue treated with a saturated solution of sodium carbonate (10 ml). Extraction with ethyl acetate, combination of the organic layers, drying over sodium sulphate, and evaporation at reduced pressure yielded the crude product. After chromatography on a silica-NH$_2$ phase using ethyl acetate as the eluent, the product was obtained as a yellowish oil which, after trituration in isopropyl ether, yielded the 5-but-2-ynyloxy-pyrazine-2-carboxylic acid [3-((R)-2-amino-5,5-difluoro-4-methyl-5,6-dihydro-4H-[1,3] oxazin-4-yl)-4-fluoro-phenyl]-amide (52 mg, 63% yield) as a white solid. MS (ISP): m/z=434.2 [M+H]$^+$.

EXAMPLE 2

[$^3$H]-5-But-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide

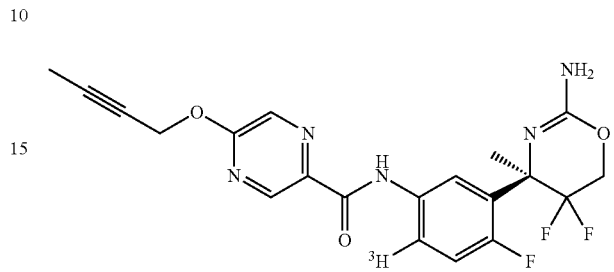

The ethanolic solution of (R)-4-(5-amino-2-fluoro-phenyl)-5,5-difluoro-4-methyl-5,6-dihydro-4H-[1,3]oxazin-2-ylamine labeled with tritium (intermediate D2) (5 ml; c=1.15 GBq/ml (31.4 mCi/ml), 5.81 GBq (157 mCi), ~1.7 mg, 0.0065 mmol) was concentrated under a flow of argon. The residue was dissolved in methanol (75 μl) to yield a light brown solution which was cooled to 0° C. (solution 1). A suspension of 5-(but-2-ynyloxy)pyrazine-2-carboxylic acid CAS[1221447-98-8] (2.4 mg, 0.012 mmol) in methanol (94 μl) was cooled to 0° C. After addition of 4-(4,6-dimethoxy [1.3.5]triazin-2-yl)-4-methylmorpholinium chloride hydrate (DMTMM) (3.7 mg, 0.013 mmol) the mixture was stirred at 0° C. for 2 hours. Thereafter, 75 μl of the suspension were added to solution 1, and the reaction mixture stirred for 15 hours while the temperature rose to 18° C. For additional 3 hours stirring was continued at room temperature. For the workup, the solvent was removed under a flow of nitrogen and the residue partitioned between ethyl acetate (1 ml) and an aqueous solution of sodium carbonate (2 N). The organic layer was washed with water (1 ml) and the aqueous phase re-extracted with ethyl acetate (2×1 ml). The combined organic layers were dried over sodium sulphate and evaporated at reduced pressure. After preparative HPLC purification (XBridge C18, 5 μm, 10×250 mm) using a mixture of pH 9 buffer, acetonitrile and water as the eluent, 3.79 GBq (103 mCi, 66% yield) of the tritiated 5-but-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide were obtained. Radio-HPLC analysis indicated a radiochemical purity of >99%. The specific activity was determined to be 980 GBq/mmol (26.5 Ci/mmol) by MS-spectroscopy.

EXAMPLE 3

5-Chloropyrazine-2-carboxylic acid

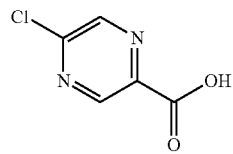

Methyl 5-chloropyrazine-2-carboxylate (CAS [33332-25-1], 1 g, 5.79 mmol) was dissolved in a mixture of THF (50 ml) and water (50 ml). Lithium hydroxide monohydrate (243 mg, 5.79 mmol) was added and the reaction mixture was stirred at RT overnight. The pH was adjusted to 1 with 1M HCl and the product was extracted with three portions of EtOAc. The combined organic layers were dried over $Na_2SO_4$ and concentrated under vacuum. The crude material was purified by flash chromatography ($SiO_2$, 50 g, 0 to 20% MeOH in DCM) to yield the title compound as white solid (741 mg, 81%). MS (ISP): m/z=159.0 $[M+H]^+$.

(R)—N-(3-(2-Amino-5,5-difluoro-4-methyl-5,6-dihydro-4H-1,3-oxazin-4-yl)-4-fluorophenyl)-5-chloropyrazine-2-carboxamide

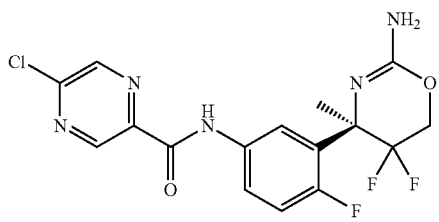 [SMILES: C[C@]1(c2cc(NC(=O)c3cnc(Cl)cn3)ccc2F)N=C(N)OCC1(F)F]

5-Chloropyrazine-2-carboxylic acid (367 mg, 2.31 mmol) was combined with MeOH (25 ml) to give a colorless solution. 4-(4,6-Dimethoxy[1.3.5]triazin-2-yl)-4-methylmorpholinium chloride hydrate (DMTMM, 705 mg, 2.55 mmol) was added at 0° C. and the solution was stirred at 0° C. for 30 min. A solution of (R)-4-(5-amino-2-fluoro-phenyl)-5,5-difluoro-4-methyl-5,6-dihydro-4H-[1,3]oxazin-2-ylamine (intermediate A 8.1, 600 mg, 2.31 mmol) in MeOH (10 ml) was added dropwise and the reaction mixture was stirred overnight at 0° C. Sat. aq. $NaHCO_3$ was added and the product was extracted with three portions of AcOEt. The combined organic layers were dried over $Na_2SO_4$ and concentrated under vacuum. The crude material was purified by flash chromatography ($SiO_2$, 50 g, 50 to 100% EtOAc in heptane). White solid (540 mg, 58%). MS (ISP): m/z=400.1 $[M+H]^+$.

((R)-4-{5-[(5-Chloro-pyrazine-2-carbonyl)-amino]-2-fluoro-phenyl}-5,5-difluoro-4-methyl-5,6-dihydro-4H-[1,3]oxazin-2-yl)-carbamic acid tert-butyl ester

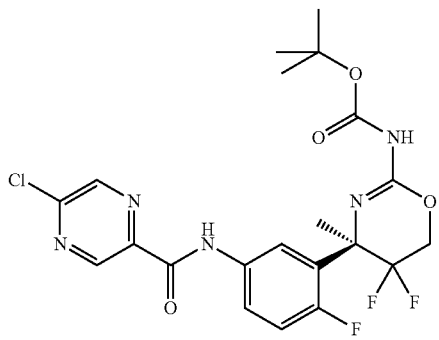 [SMILES: CC(C)(C)OC(=O)NC1=N[C@](C)(c2cc(NC(=O)c3cnc(Cl)cn3)ccc2F)C(F)(F)CO1]

(R)—N-(3-(2-Amino-5,5-difluoro-4-methyl-5,6-dihydro-4H-1,3-oxazin-4-yl)-4-fluorophenyl)-5-chloropyrazine-2-carboxamide (540 mg, 1.35 mmol) was combined with DCM (15 ml) to give a colorless solution. $Boc_2O$ (310 mg, 1.42 mmol) was added at 0° C. and the mixture was stirred 1 h at this temperature. After warming to RT, stirring was continued for 5 h. More $Boc_2O$ (310 mg, 1.42 mmol) was added and the reaction mixture was stirred overnight. A third portion of $Boc_2O$ (310 mg, 1.42 mmol) was then added and stirring continued for one more day. After dilution of the mixture with sat. aq. $NaHCO_3$ the product was extracted with DCM (3 portions). The organic layers were dried over $Na_2SO_4$ and concentrated under vacuum. The crude material was purified by flash chromatography ($SiO_2$, 50 g, 0 to 100% EtOAc in heptane). White solid (405 mg, 60%). MS (ISP): m/z=500.2 $[M+H]^+$.

((R)-5,5-Difluoro-4-{2-fluoro-5-[(5-prop-2-ynyloxy-pyrazine-2-carbonyl)-amino]-phenyl}-4-methyl-5,6-dihydro-4H-[1,3]oxazin-2-yl)-carbamic acid tert-butyl ester

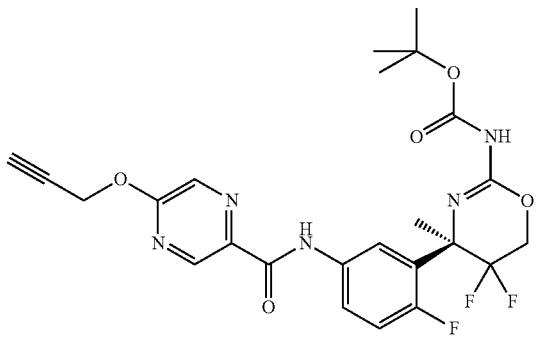 [SMILES: C#CCOc1cnc(C(=O)Nc2ccc(F)c([C@@]3(C)N=C(NC(=O)OC(C)(C)C)OCC3(F)F)c2)cn1]

((R)-4-{5-[(5-Chloro-pyrazine-2-carbonyl)-amino]-2-fluoro-phenyl}-5,5-difluoro-4-methyl-5,6-dihydro-4H-[1,3]oxazin-2-yl)-carbamic acid tert-butyl ester (400 mg, 800 µmol) was combined with DMF (1.2 ml) to give a colorless solution. KOtBu (180 mg, 1.6 mmol) and propargyl alcohol (449 mg, 477 µl, 8.00 mmol) were added and the reaction mixture was stirred 2 h at RT. Water was carefully added and the product was extracted with EtOAc. The organic layers were dried over $Na_2SO_4$ and concentrated under vacuum. The crude material was purified by flash chromatography ($SiO_2$, 20 g, 0 to 50% EtOAc in heptane). Light yellow solid (350 mg, 84%). MS (ISP): m/z=520.2 $[M+H]^+$.

(R)—N-(3-(2-Amino-5,5-difluoro-4-methyl-5,6-dihydro-4H-1,3-oxazin-4-yl)-4-fluorophenyl)-5-(prop-2-ynyloxy)pyrazine-2-carboxamide

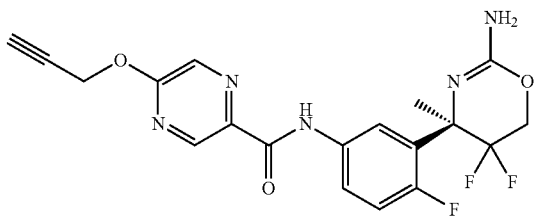 [SMILES: C#CCOc1cnc(C(=O)Nc2ccc(F)c([C@@]3(C)N=C(N)OCC3(F)F)c2)cn1]

((R)-5,5-Difluoro-4-{2-fluoro-5-[(5-prop-2-ynyloxy-pyrazine-2-carbonyl)-amino]-phenyl}-4-methyl-5,6-dihydro-4H-[1,3]oxazin-2-yl)-carbamic acid tert-butyl ester (350 mg, 674 μmol) was combined with DCM (5.2 ml) to give a light yellow solution. The solution was cooled to 0° C. and TFA (768 mg, 519 μl, 6.74 mmol) was added. After stirring 30 min at 0° C. the ice bath was removed and the reaction was allowed to warm up and was stirred at RT for 6 h. The pH of the reaction mixture was adjusted to 8 by dropwise addition of sat. aq. NaHCO$_3$ and the product was extracted with DCM. The organic layers were dried over Na$_2$SO$_4$ and concentrated under vacuum. A colorless foam was obtained that was purified by flash chromatography (SiO$_2$, 10 g, 0 to 80% EtOAc in heptane). Colorless foam (230 mg, 81%). MS (ISP): m/z=420.1 [M+H]$^+$.

(R)—N-(3-(2-Amino-5,5-difluoro-4-methyl-5,6-dihydro-4H-1,3-oxazin-4-yl)-4-fluorophenyl)-5-(3-(tributylstannyl)prop-2-ynyloxy)pyrazine-2-carboxamide

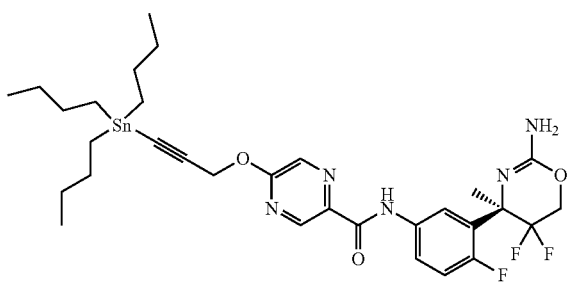 [SMILES: CCC[CH2][Sn]([C]#CCOc1cnc(C(=O)Nc2ccc(F)c([C@@]3(C)N=C(N)OCC3(F)F)c2)cn1)([CH2]CCC)[CH2]CCC]

(R)—N-(3-(2-Amino-5,5-difluoro-4-methyl-5,6-dihydro-4H-1,3-oxazin-4-yl)-4-fluorophenyl)-5-(prop-2-ynyloxy)pyrazine-2-carboxamide (170 mg, 405 μmol) was combined with tri-n-butyltinmethoxide (651 mg, 586 μl, 2.03 mmol) and heated to 60° C. for 6 hours. The reaction mixture was allowed to cool to RT and purified by flash chromatography (SiO$_2$, 20 g, 0 to 50% EtOAc in heptane) to yield the title compound (195 mg, 68%) as a colorless oil. MS (ISP): m/z=710.2 [M+H]$^+$.

[$^{11}$C]-5-But-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide

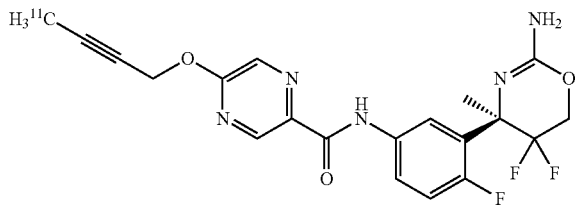 [SMILES: C[C@]1(c2cc(NC(=O)c3cnc(OCC#C[11CH3])cn3)ccc2F)N=C(N)OCC1(F)F]

[Pd(tBu$_3$)$_2$] (2.05 mg, 2.89 μl) was dissolved in DMF (200 μl) in a septum sealed vial. [$^{11}$C]Methyl iodide (prepared according to Larsen, P., Ulin, J., Dahlstrom, K., *J. Label. Compds. Radiopharm.* 37, 73-75, 1995) was transferred in a stream of helium (30 mL/min) into the vial via a cannula. Once the radioactivity had plateaued, the solution was left at room temperature for 4 minutes after which a solution of 2.03 mg of (R)—N-(3-(2-amino-5,5-difluoro-4-methyl-5,6-dihydro-4H-1,3-oxazin-4-yl)-4-fluorophenyl)-5-(3-(tributylstannyl)prop-2-ynyloxy)pyrazine-2-carboxamide in DMF (100 μL) was added and the reaction continued for another 4 minutes at room temperature. The reaction mixture was diluted in 10 mL of triethylamine buffer (pH 7.2) and passed through a Water C18 SepPak Plus. The SepPak was washed with 10 mL of 10:90 acetonitrile:triethylamine buffer (pH 7.2). The crude product was eluted from the SepPak with 1 mL of pure acetonitrile, mixed with 0.5 mL of triethylamine buffer (pH 7.2) and transferred to semipreparative HPLC for purification using Waters XBridge C18 10μ (150×10 mm) column with 40% acetonitrile: 60% triethylamine buffer (pH 7.2).

The product fraction as determined with an in-line radiometric detector was collected in a reservoir of water. The reservoir was pressurized to load the product onto the C18 Sep-Pak. The C18 Sep-Pak was then washed with 10 mL 0.9% Sodium Chloride Injection. The final product was eluted from the C18 Sep-Pak with 1 mL of Ethanol followed by 10 mL of 0.9% Sodium Chloride Injection, through a sterilizing 0.22μ filter in a sterile, pyrogen-free vial that had been preloaded with 4 mL Sodium Chloride Injection. In this particular experiment, 24 mCi of final product was obtained 33 minutes after trapping approx. 600 mCi of [$^{11}$C]methyl iodide. The calculated specific activity at end-of-synthesis was over 5900 mCi per micromole with a radiochemical purity of 100%. HPLC Conditions: Analytical: Waters Xbridge 4.6×100 mm, 3.5 μm, 40/60 MeCN/TEA Buffer pH 7.2, 2 mL/min, UV@ 254 nm. Semi-Prep: Waters Xbridge 10×150 mm, 10 μm, 40/60 MeCN/TEA Buffer pH 7.2, 10 mL/min, UV@254 nm.

The invention claimed is:

1. A compound of formula I,

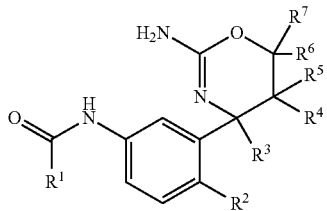

wherein

R$^1$ is aryl or heteroaryl, each substituted by 1-4 substituents individually selected from halogen-C$_{2-6}$-alkenyl, halogen-C$_{2-6}$-alkynyl, C$_{1-6}$-alkoxy-C$_{2-6}$-alkenyl, C$_{1-6}$-alkoxy-C$_{2-6}$-alkynyl, C$_{2-6}$-alkenyl-C$_{1-6}$-alkoxy and C$_{2-6}$-alkynyl-C$_{1-6}$-alkoxy;

R$^2$ is halogen;

R$^3$ is C$_{1-6}$-alkyl;

R$^4$ is selected from the group consisting of
  i) hydrogen,
  ii) C$_{1-6}$-alkyl, and
  iii) halogen;

R$^5$ is selected from the group consisting of
  i) hydrogen,
  ii) C$_{1-6}$-alkyl, and
  iii) halogen;

R$^6$ is selected from the group consisting of
  i) hydrogen, and
  ii) C$_{1-6}$-alkyl;

R$^7$ is selected from the group consisting of
  i) hydrogen, and
  ii) C$_{1-6}$-alkyl;

and when R$^1$ is heteroaryl substituted by C$_{2-6}$-alkynyl-C$_{1-6}$-alkoxy, then R$^4$ and R$^5$ are both hydrogen or are both halogen;

or pharmaceutically acceptable salts thereof.

2. The compound according to claim 1, wherein $R^1$ is heteroaryl substituted by halogen-$C_{2-6}$-alkenyl, halogen-$C_{2-6}$-alkynyl, $C_{1-6}$-alkoxy-$C_{2-6}$-alkenyl, $C_{1-6}$-alkoxy-$C_{2-6}$-alkynyl, $C_{2-6}$-alkenyl-$C_{1-6}$-alkoxy or $C_{2-6}$-alkynyl-$C_{1-6}$-alkoxy.

3. The compound according to claim 1, wherein $R^1$ is pyrazinyl substituted by halogen-$C_{2-6}$-alkenyl, halogen-$C_{2-6}$-alkynyl, $C_{1-6}$-alkoxy-$C_{2-6}$-alkenyl, $C_{1-6}$-alkoxy-$C_{2-6}$-alkynyl, $C_{2-6}$-alkenyl-$C_{1-6}$-alkoxy or $C_{2-6}$-alkynyl-$C_{1-6}$-alkoxy.

4. The compound according to claim 1, wherein $R^1$ is $C_{2-6}$-alkynyl-$C_{1-6}$-alkoxy-pyrazinyl.

5. The compound according to claim 1, wherein $R^2$ is F.

6. The compound according to claim 1, wherein $R^3$ is methyl.

7. The compound according to claim 1, wherein $R^4$ and $R^5$ are both halogen.

8. The compound according to claim 1, wherein $R^4$ and $R^5$ are both F.

9. The compound according to claim 1, wherein $R^6$ and $R^7$ are both hydrogen.

10. The compound according to claim 1, wherein $R^1$ is 5-but-2-ynyloxy-pyrazinyl.

11. The compound according to claim 1, which is 5-But-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide.

12. The compound according to claim 1, which is a Tritium-labelled compound of formula Ia, wherein $R^1$, $R^2$, $R^3$, $R^4$, $R^5$, $R^6$ and $R^7$ have the meanings according to claim 1,

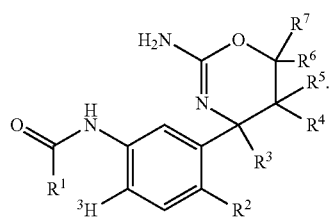

Ia

13. A Tritium labelled compound of formula Ia according to claim 12, which is [$^3$H]-5-But-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide.

14. The compound according to claim 1, which is a $^{11}$C-labelled compound of formula Ia', wherein $R^2$, $R^3$, $R^4$, $R^5$, $R^6$ and $R^7$ have the meanings according claim 1,

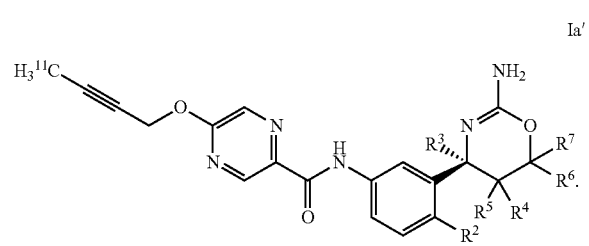

Ia'

15. A $^{11}$C-labelled compound of formula Ia' according to claim 14, which is [$^{11}$C]-5-But-2-ynyloxy-pyrazine-2-carboxylic acid [3-((R)-2-amino-5,5-difluoro-4-methyl-5,6-dihydro-4H-[1,3]oxazin-4-yl)-4-fluoro-phenyl]-amide.

16. A method for diagnostic imaging of the BACE1 enzyme which comprises administering to a mammal an effective amount of a compound according to claim 1.

17. A pharmaceutical composition, comprising a therapeutically effective amount of a compound according to claim 1 and a pharmaceutically acceptable carrier and/or a pharmaceutically acceptable auxiliary substance.

18. A method of treating diseases and disorders characterized by elevated β-amyloid levels or β-amyloid oligomers or β-amyloid plaques and further deposits, Alzheimer's disease, diabetes or type 2 diabetes, comprising the steps of administering a compound according to claim 1 to a human being or animal in need thereof.

* * * * *

UNITED STATES PATENT AND TRADEMARK OFFICE
CERTIFICATE OF CORRECTION

PATENT NO. : 9,073,909 B2
APPLICATION NO. : 14/118754
DATED : July 7, 2015
INVENTOR(S) : Edilio Boroni et al.

Page 1 of 1

It is certified that error appears in the above-identified patent and that said Letters Patent is hereby corrected as shown below:

Title Page (75) fourth Inventor's name to read as follows:

--Dieter Muri, Basel (CH)--

Signed and Sealed this
Nineteenth Day of January, 2016

Michelle K. Lee
*Director of the United States Patent and Trademark Office*